(12) United States Patent
Biedermann et al.

(10) Patent No.: US 11,076,895 B2
(45) Date of Patent: Aug. 3, 2021

(54) INSTRUMENT FOR LOCKING AND UNLOCKING A HEAD OF A BONE ANCHOR IN A POLYAXIAL BONE ANCHORING DEVICE

(71) Applicant: BIEDERMANN TECHNOLOGIES GMBH & CO. KG, Donaueschingen (DE)

(72) Inventors: Timo Biedermann, Trossingen (DE); Kevin Dold, Horb am Neckar (DE); Achim Schünemann, VS-Mühlhausen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 118 days.

(21) Appl. No.: 16/571,858

(22) Filed: Sep. 16, 2019

(65) Prior Publication Data

US 2020/0078056 A1    Mar. 12, 2020

Related U.S. Application Data

(63) Continuation of application No. 15/669,604, filed on Aug. 4, 2017, now Pat. No. 10,470,805.

(30) Foreign Application Priority Data

Aug. 24, 2016  (EP) .................................... 16185546

(51) Int. Cl.
*A61B 17/70*  (2006.01)
(52) U.S. Cl.
CPC ........ *A61B 17/7083* (2013.01); *A61B 17/708* (2013.01); *A61B 17/7032* (2013.01);
(Continued)

(58) Field of Classification Search
CPC ....................................... A61B 17/7074–7092
See application file for complete search history.

(56) References Cited

U.S. PATENT DOCUMENTS 6,440,142 B1   8/2002  Ralph et al.
8,192,438 B2 *  6/2012  Garamszegi ....... A61B 17/7086
                                                606/86 A
(Continued)

FOREIGN PATENT DOCUMENTS

CN    103027732 A    4/2013
CN    104363846 A    2/2015

OTHER PUBLICATIONS

European Search Report for European Application No. 16185546.5 dated Feb. 7, 2017 and dated Feb. 15, 2017 (9 pages).

*Primary Examiner* — Eduardo C Robert
*Assistant Examiner* — Steven J Cotroneo
(74) *Attorney, Agent, or Firm* — Lewis Roca Rothgerber Christie LLP

(57) ABSTRACT

An instrument for locking and unlocking a head of a bone anchor relative to a receiving part of a polyaxial bone anchoring device includes a tube assembly with an inner tube and an outer tube at least partially around the inner tube, and an actuator assembly including an actuating mechanism movable from a first orientation to a second orientation to displace the inner tube and the outer tube relative to one another between a first axial position configured to unlock the bone anchoring device such that the head is pivotable relative to the receiving part, and a second axial position configured to lock the head. The actuator assembly is adjustable between a first configuration where the tube assembly assumes the first axial position when the actuating mechanism is moved, and a second configuration where the
(Continued)

tube assembly assumes the second axial position when the actuating mechanism is moved.

20 Claims, 10 Drawing Sheets

Related U.S. Application Data

(60) Provisional application No. 62/379,108, filed on Aug. 24, 2016.

(52) U.S. Cl.
CPC ...... *A61B 17/7037* (2013.01); *A61B 17/7076* (2013.01); *A61B 17/7079* (2013.01); *A61B 17/7082* (2013.01)

(56) References Cited

U.S. PATENT DOCUMENTS

| | | | |
|---|---|---|---|
| 9,655,664 | B2 | 5/2017 | Barrus et al. |
| 2004/0147937 | A1 | 7/2004 | Dunbar, Jr. et al. |
| 2005/0131408 | A1* | 6/2005 | Sicvol ................ A61B 17/8605 606/86 A |
| 2005/0149048 | A1* | 7/2005 | Leport .................. A61B 17/88 606/99 |
| 2005/0228392 | A1 | 10/2005 | Keyer et al. |
| 2005/0261702 | A1 | 11/2005 | Oribe et al. |
| 2006/0200132 | A1 | 9/2006 | Chao et al. |
| 2007/0093817 | A1* | 4/2007 | Barrus ............... A61B 17/7037 606/264 |
| 2008/0077135 | A1 | 3/2008 | Stad et al. |
| 2008/0172062 | A1* | 7/2008 | Donahue ........... A61B 17/7038 606/104 |
| 2008/0243133 | A1 | 10/2008 | Heinz |
| 2009/0088764 | A1* | 4/2009 | Stad .................. A61B 17/8875 606/90 |
| 2009/0105712 | A1 | 4/2009 | Dauster et al. |
| 2011/0118791 | A1 | 5/2011 | Nunley et al. |
| 2011/0202096 | A1 | 8/2011 | White et al. |
| 2012/0078308 | A1* | 3/2012 | Dziedzic ............ A61B 17/7086 606/264 |
| 2012/0123487 | A1 | 5/2012 | Mahar |
| 2012/0191144 | A1* | 7/2012 | Peultier .............. A61B 17/7086 606/86 A |
| 2013/0085536 | A1* | 4/2013 | Biedermann ...... A61B 17/7035 606/308 |
| 2013/0110179 | A1 | 5/2013 | Barrus et al. |
| 2014/0163617 | A1 | 6/2014 | Boachie-Adjei et al. |
| 2014/0236236 | A1 | 8/2014 | Krüger |
| 2014/0276896 | A1 | 9/2014 | Harper |
| 2015/0351810 | A1 | 12/2015 | Lindner et al. |
| 2015/0359572 | A1 | 12/2015 | Reimels et al. |

* cited by examiner

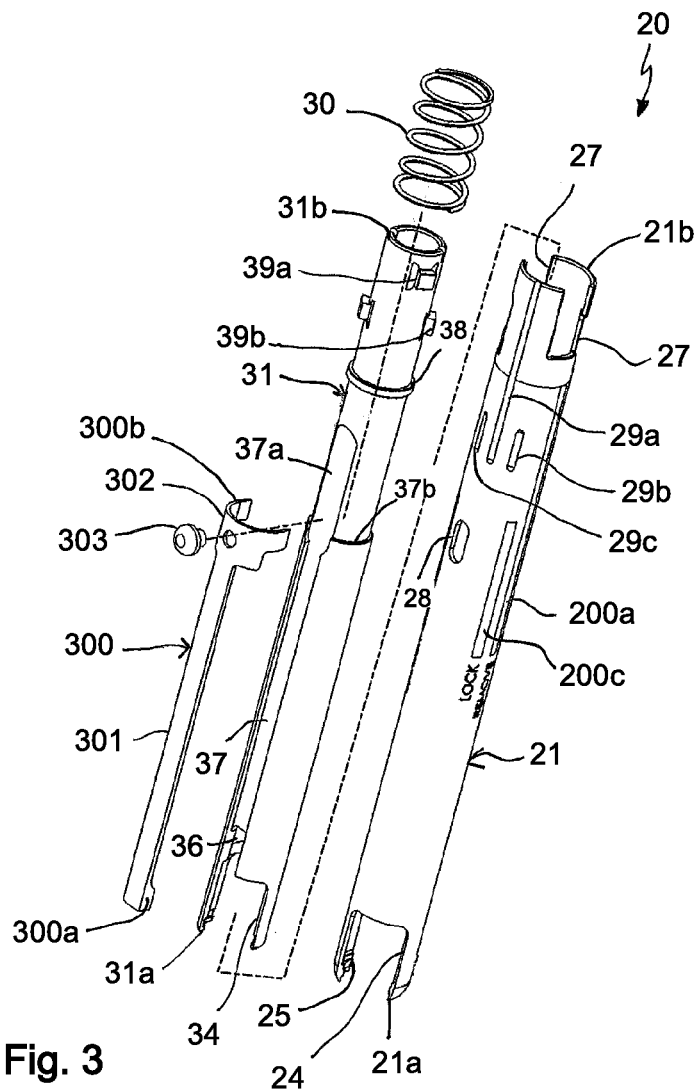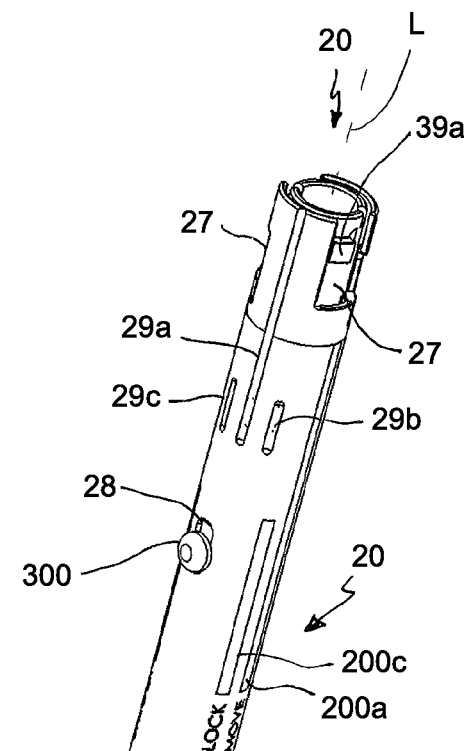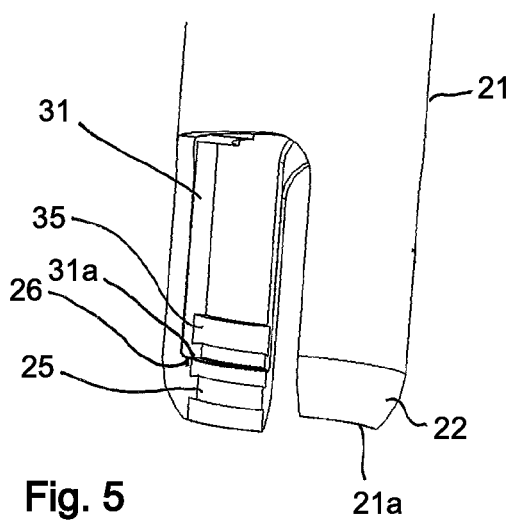
Fig. 3
Fig. 5
Fig. 4

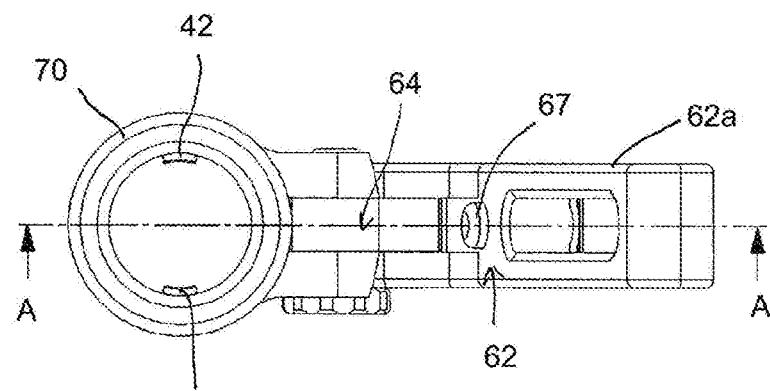
Fig. 10
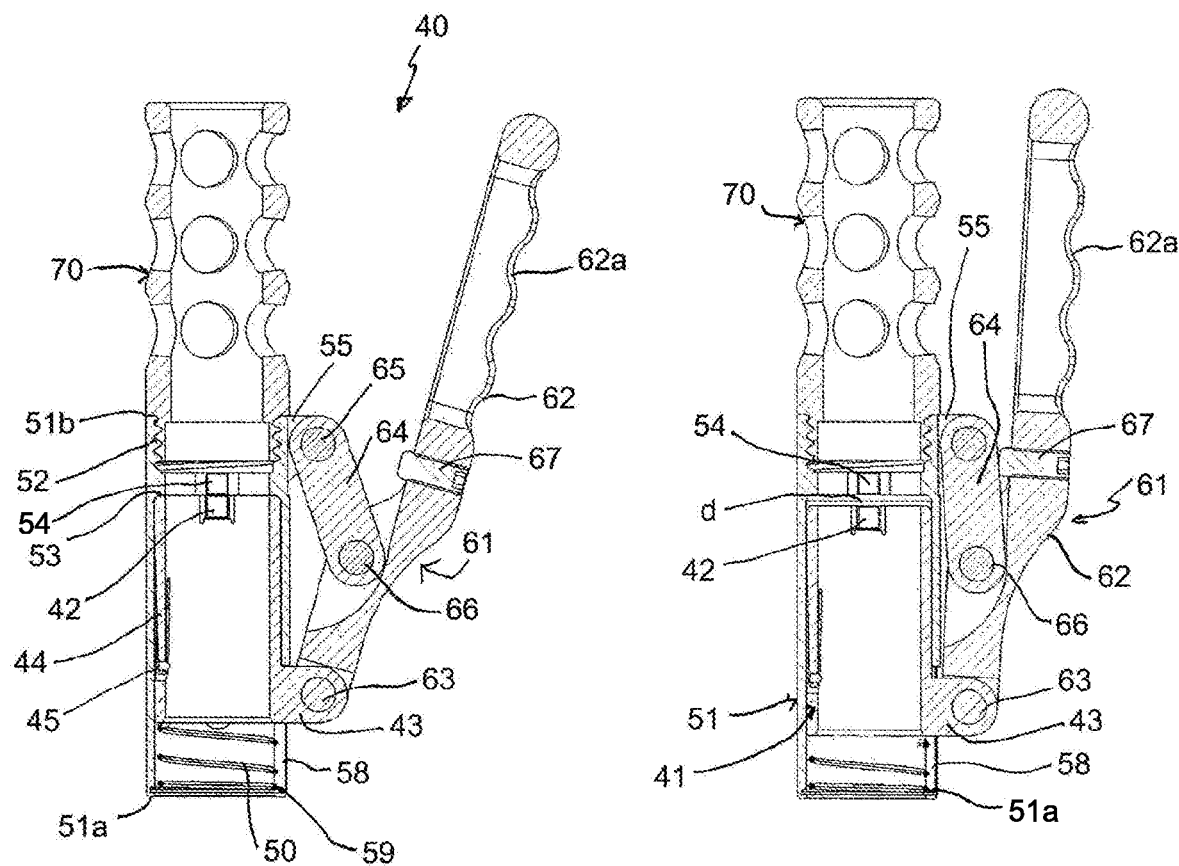
Fig. 11a
Fig. 11b

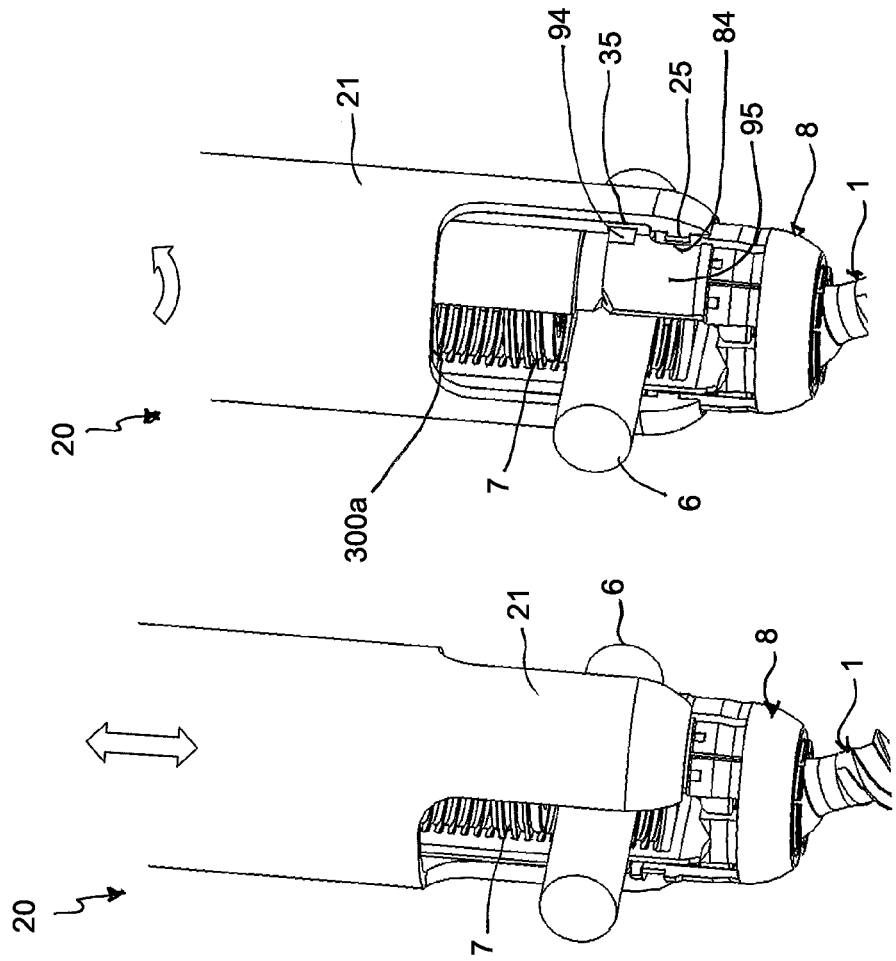

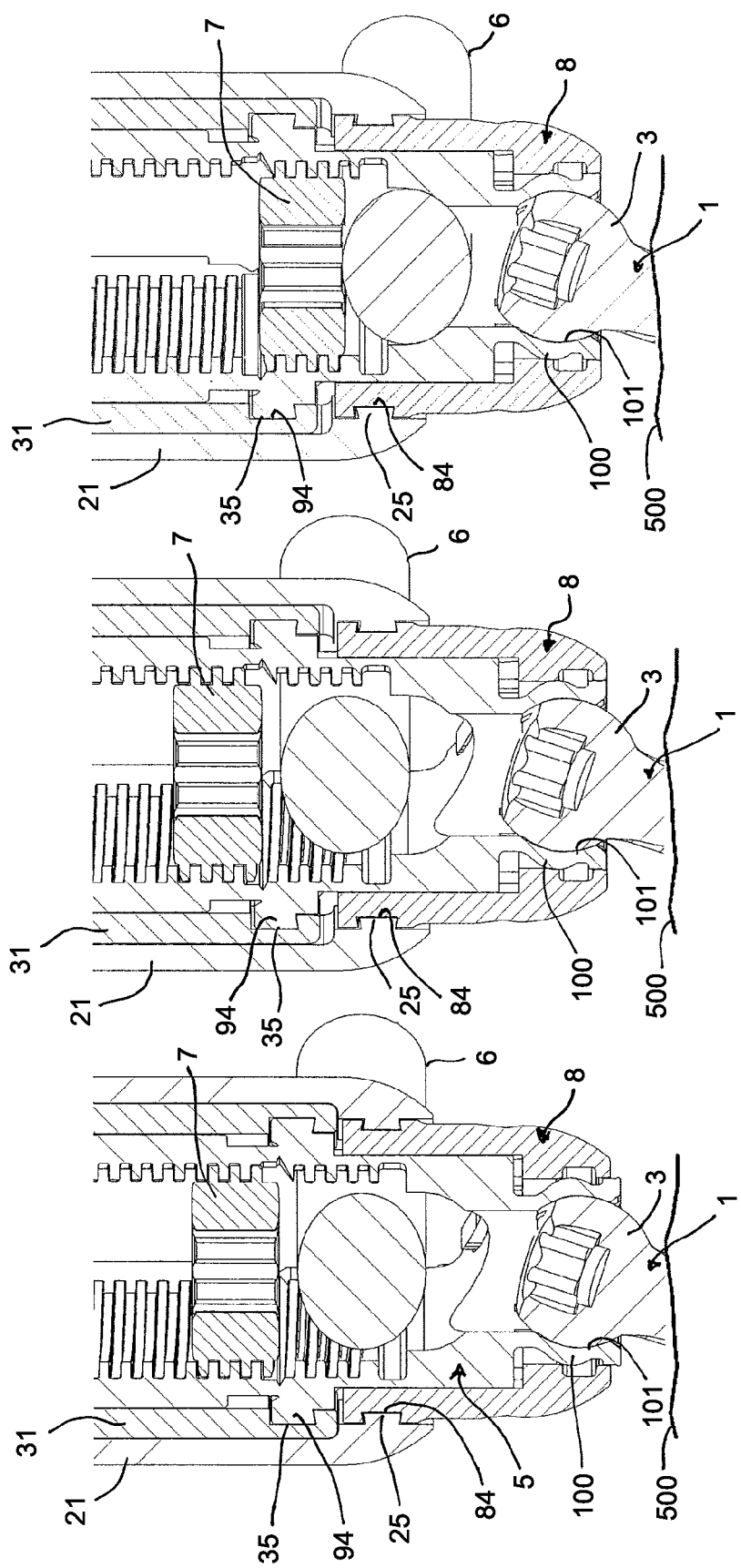

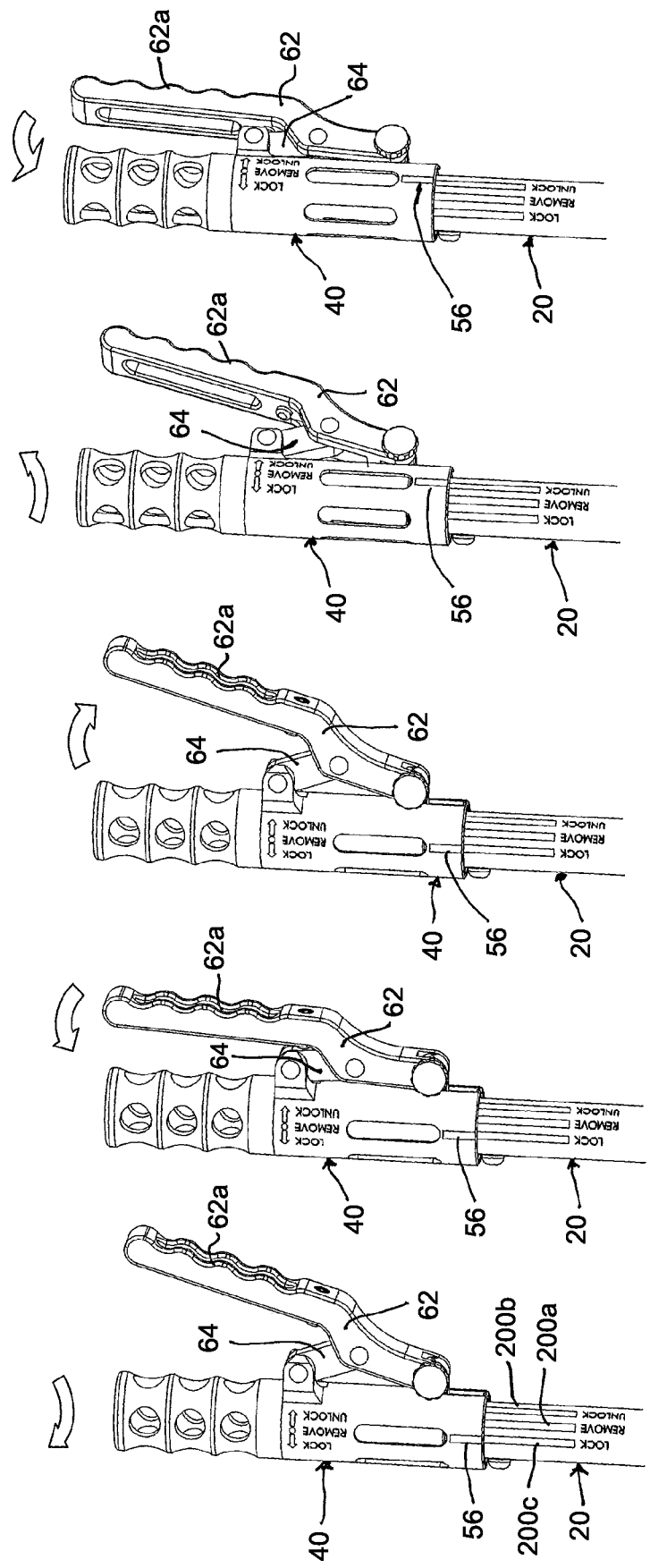

INSTRUMENT FOR LOCKING AND UNLOCKING A HEAD OF A BONE ANCHOR IN A POLYAXIAL BONE ANCHORING DEVICE

CROSS-REFERENCE TO RELATED APPLICATION(S)

This application a continuation of U.S. patent application Ser. No. 15/669,604, filed Aug. 4, 2017, which claims the benefit of U.S. Provisional Patent Application Ser. No. 62/379,108, filed Aug. 24, 2016, and claims priority from European Patent Application EP 16 185 546.5, filed Aug. 24, 2016, the contents of which are hereby incorporated by reference in their entirety.

BACKGROUND

Field

The invention relates to an instrument for locking and unlocking a head of a bone anchor in a polyaxial bone anchoring device. The instrument comprises a tube assembly with an inner tube and an outer tube that are displaceable relative to each other for independently locking and unlocking the head and an actuator assembly for actuating the tube assembly. Such an instrument is particularly applicable to a polyaxial bone anchoring device that has a receiving part with a head receiving portion for receiving the head of the bone anchor and an outer locking ring for locking the head.

Description of Related Art

U.S. 2013/0085536 A1 describes a polyaxial bone anchoring device including a receiving part with a rod receiving portion and head receiving portion for introducing and clamping of the head and a locking ring configured to be arranged around the head receiving portion. The locking ring includes an engagement structure for engagement with a tool to allow the locking ring to be moved out of the locking position, i.e. releasing the locking mechanism. The tool comprises a tubular member that is configured to engage the locking ring and a shaft acting on the receiving part. In one embodiment, unlocking of the head may be carried out while the rod is inserted.

U.S. 2013/0110179 A1 describes a set comprising a locking device and a separate unlocking device for locking and unlocking a multi-planar, taper lock screw.

SUMMARY

In spinal surgery often multiple segments of the spinal column have to be corrected and/or stabilized using a spinal rod and polyaxial bone anchors. During such a procedure repeated adjustments of bone anchoring elements and the rod relative to receiving parts of polyaxial bone anchoring devices may become necessary.

Embodiments of the invention provide an improved instrument for carrying out revisions or further positioning or repositioning of a polyaxial bone anchoring device with respect to a rod during surgery that is simple to handle for a user and that permits a greater variety of correction steps during surgery. It is a further object to provide a system of such an instrument and a polyaxial bone anchoring device adapted for use with the instrument.

With the instrument the correction steps that are necessary for adjusting the bone anchoring elements and the rod and also the adjustment of the position of one or more vertebrae are simplified. In a first aspect, a temporary locking of the bone anchoring element in the receiving part can be effected using only the instrument with the rod already inserted into the receiving part but without the aid of a locking element such as a set screw. As a result thereof, the polyaxial bone anchoring device allows to adjust or re-adjust an angular position of the receiving part relative to the bone anchoring device several times while the rod is already inserted. The temporary locking of the head using the instrument also permits to use the polyaxial bone anchoring device like a monoaxial bone anchoring device.

The receiving part of the polyaxial bone anchoring device may comprise extended tabs that allow the rod during the adjustment step to be on a position higher above the head compared to a receiving part without extended tabs. Hence, with the instrument, it is also possible to correct a position of a vertebra in that the polyaxial bone anchoring device together with the associated vertebra is pulled against the rod.

The instrument can be easily switched between an unlocking configuration in which the instrument allows pivoting of the head in the receiving part and a locking configuration in which the instrument effects a locking of the head in the receiving part and vice-versa. The switching can be effected by rotating the actuator assembly. An actuating mechanism of the actuator assembly of the instrument is designed such that the locking and unlocking of the head can be effected by the same grasping movement of a user. Hence, the operation of the instrument is easy to learn and memorize, and the risk of operating errors is reduced which results in an enhanced safety during surgery.

In a further aspect, the actuator assembly may be removably connectable to the tube assembly, Thereby it is possible to adjust a plurality of polyaxial bone anchoring devices that each are connected to a tube assembly with one single actuator assembly one after the other. As the tube assemblies may be positioned close to each other, operating with one single actuator assembly is convenient in view of the reduced available space. The tube assemblies may be all the same or differ with respect to their length or other features such as the engagement features for engagement with the polyaxial bone anchoring device. Hence, the instrument may also provide a modular system that includes an actuator assembly and different tube assemblies that are adapted to be used with the actuator assembly.

The instrument may additionally produce a tactile or audible sign when it enters one of the different configurations of locking, unlocking, or removing. This further increases the safety and user-friendliness.

BRIEF DESCRIPTION OF THE DRAWINGS

Further features and advantages of the invention will become apparent from the description of embodiments by means of the accompanying drawings. In the drawings:

FIG. 3 shows an exploded perspective view of the tube assembly of the instrument of FIGS. 1 and 2.

FIG. 4 shows a perspective view of the tube assembly of FIG. 3 in an assembled state.

FIG. 5 shows an enlarged perspective view of a front portion of the tube assembly of FIG. 4 in the assembled state.

FIG. 10 shows a top view of the actuator assembly of FIGS. 8 and 9.

FIG. 11a shows a cross-sectional view along line A-A in FIG. 10 of the actuator assembly of FIGS. 8 to 10 in the configuration shown in FIG. 9.

FIG. 11b shows a cross-sectional view along line A-A in FIG. 10 of the actuator assembly of FIGS. 8 to 10 in a straight configuration of the lever assembly.

FIGS. 15a to 15c show perspective views of steps of connecting the instrument to the polyaxial bone anchoring device according to an embodiment.

FIGS. 16a to 16c show cross-sectional views of steps of actuating a locking ring of the polyaxial bone anchoring device relative to the receiving part using the instrument according to an embodiment, wherein the cross-section is taken in a plane extending through the central axis of the receiving part and at an angle of about 45° relative to an axis of an inserted rod.

FIGS. 17a to 17e show perspective views of steps of operating the instrument according to an embodiment.

DETAILED DESCRIPTION

Figure 1:
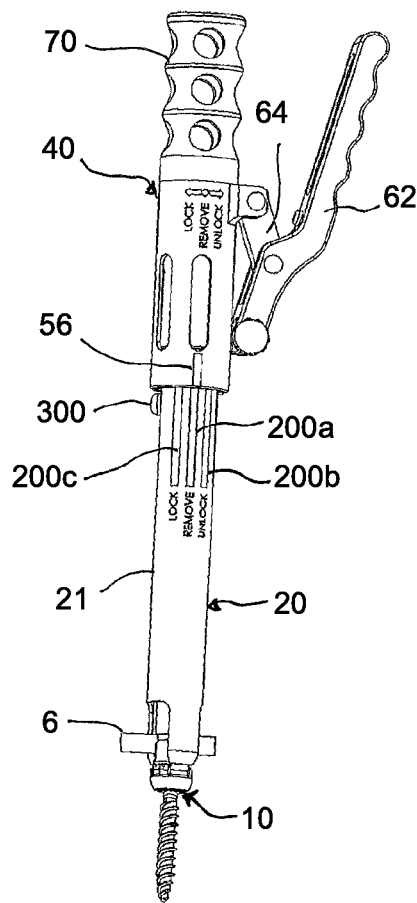
FIG. 1 shows a perspective view of an instrument according to an embodiment.
Figure 2:
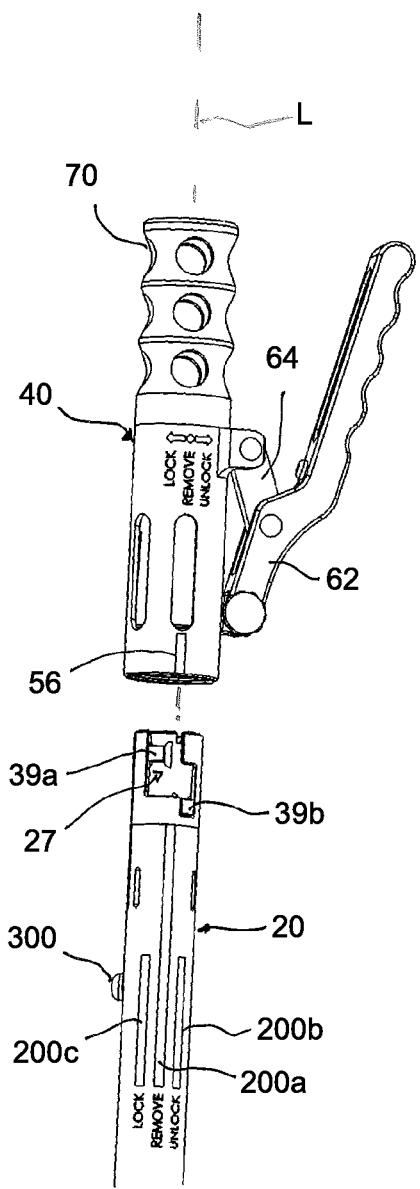
FIG. 2 shows an exploded perspective view of the instrument of FIG. 1.

Referring to FIGS. 1 to 3, in one embodiment, the instrument comprises a tube assembly 20 and an actuator assembly 40 that is removably connectable to the tube assembly 20. As shown in FIG. 1, the tube assembly 20 is connectable to a polyaxial bone anchoring device 10.

The tube assembly 20 includes an outer tube 21 and an inner tube 31 and a longitudinal axis or tube axis L. The outer tube 21 and the inner tube 31 are in the assembled state axially displaceable relative to each other along the longitudinal axis L to a certain extent that permits to move a portion of the polyaxial bone anchoring device from an unlocking position of a bone anchoring device to a locking position of the bone anchoring device and vice-versa. The displacement of the inner tube 31 and the outer tube 21 relative to each other is effected by the actuator assembly 40 as explained below.

As shown more in detail in FIGS. 2 to 5, the outer tube 21 comprises a front end 21a and a rear end 21b opposite to the front end 21a. A front portion of the instrument adjacent to the front end 21a may taper in a section 22 towards the front end 21a to reduce an overall space needed by the instrument when attached to the polyaxial bone anchoring device 10.

A recess 24 is formed that extends from the front end 21a of the outer tube 21 to a distance thereof. The recess 24 has a width in the circumferential direction that is larger than an upper width of the polyaxial bone anchoring device 10 and a height that permits a rod 6 as shown in FIG. 1 to extend therethrough and to be movable in an axial direction within the recess 24 (FIG. 1). At a distance from the front end 21a of the outer tube 21 an engagement portion 25 that is adapted to engage a corresponding engagement portion of the polyaxial bone anchoring device 10 is provided. The engagement portion 25 may be in the form of a circumferentially extending rib that cooperates with a corresponding groove at the polyaxial bone anchoring device 10. At a distance towards the rear end 21b of the outer tube, a stepped portion or circumferentially extending shoulder 26 is provided that forms an abutment for the inner tube 31.

As best seen in FIGS. 3, 4 and 7a, 7b, adjacent to the rear end 21b of the outer tube 21 a cut-out or recess 27 is formed on each side of the longitudinal axis L wherein the recess 27 extends to a distance from the rear end 21b. Each recess 27 has in a perspective view, seen in FIGS. 7a and 7b, a substantially step-like shape forming a first recess area 27a that is open to the rear end 21b and adjacent thereto in a circumferential direction a second recess area 27b that has a smaller width and extends from a distance from the rear end 21b farther down, i.e. towards the front end 21a compared to the first recess area 27a. The recess 27 has the function to accommodate driving portions of the actuator assembly and driven portions from the inner tube 31 therein. The orientation of the recess 27 is such that the recess 27 is substantially aligned with the engagement portion 25 at the front end 21a.

At a distance from the rear end 21b an elongate hole 28 is provided in the outer tube 21 wherein the longer axis of the elongate hole 28 is parallel to the longitudinal axis L. The elongate hole 28 is located at a circumferential position slightly offset from the middle of the recess 24 at the front end 21a. Through the elongate hole 28 a pin connected to a stopper member may pass to enable a limited motion of the stopper member.

In addition, longitudinally extending substantially parallel grooves 29a, 29b, 29c are provided in the outer surface of the outer tube 21. The grooves 29a, 29b, 29c serve for receiving a pin of the actuator assembly to provide a tactile and/or audible sign when the actuator assembly assumes different rotational positions corresponding to locking and unlocking of a head of a bone anchoring element or removal of the actuator assembly. The middle groove 29a may extend up to the rear end 21b. Moreover, position markings 200a, 200b, 200c that extend parallel to the longitudinal axis L are provided at an outer surface of the outer tube 21. The position markings 200a, 200b, 200c are at a circumferential position of approximately that of the engagement portions of the outer tube 21 and serve for indicating in cooperation with a marking on the actuator assembly 40 to indicate an actuating position of locking or unlocking (markings 200c, 200b, respectively) or removing (marking 200a) of the actuator assembly 40. The middle marking 200a indicating the removing position may be longer than the other markings.

Turning now again to FIG. 3, the inner tube 31 comprises a front end 31a and a rear end 31b. An inner diameter of the inner tube 31 is such that a fixation element such as a set screw or a further instrument can pass through. In a front portion adjacent to the front end 31a a recess 34 is formed that substantially corresponds to the recess 24 of the outer tube 21, such that when the inner tube 31 is in the outer tube 21 the recesses 24 and 34 are aligned. At a distance from the front end 31a an engagement structure 35 is provided that is configured to cooperate with a corresponding engagement structure at the polyaxial bone anchoring device. The engagement structure 35 in the embodiment shown is a circumferentially extending groove that may cooperate with a circumferentially extending rib at the polyaxial bone anchoring device. At an end of the recess 34 opposite to the front portion 31a and located in a circumferential direction only at one side of the recess 34 a further recess or cut-out 36 extends deeper into the inner tube 31 in an axial direction. The cut-out 36 serves for accommodating an end portion of a stopper member 300 explained below. From the end of the recess 36 a recessed surface portion 37 is provided in the outer surface of the inner tube 31. The recessed surface portion 37 is elongated in an axial direction and formed and sized so as to receive and guide the stopper member 300 therein. The recessed surface portion 37 may also have a widened end portion 37a in a direction towards the rear end 31b. At around or slightly above the widened end portion 37a a circumferentially extending outer narrow shoulder 37b is provided that forms an abutment for the stopper member 300. Spaced apart from the shoulder 37b is an annular protrusion 38 that serves for axially supporting a spring element 30, for example a coil spring, that acts onto the stopper member 300.

In the upper region of the inner tube 31 first protrusions 39a, 39b are formed that serve as driven portions that are driven by driving portions of the actuator assembly 40 to displace the inner tube 31 relative to the outer tube 21. Two sets of first protrusions 39a, 39b are provided at opposite sides from the longitudinal axis L. As depicted in FIGS. 3, 4 and 7a, 7b, one protrusion 39a is located at a first distance from the rear end 31b and the other protrusion 39b is provided at a second distance greater than the first distance from the rear end 31b and is circumferentially offset from the protrusion 39a. The protrusions 39a, 39b may have approximately a square-shaped contour and may have such a height that they are substantially flush with the outer cylindrical surface of the outer tube 21 when the inner tube 31 and the outer tube 21 are assembled. As depicted more in detail in FIGS. 7a and 7b, in the assembled state, the protrusion 39a that is closer to the rear end 31a of the inner tube 31 is located in the first recess area 27a of the recess 27 of the outer tube and the second protrusion 39b is located in the lowermost portion of the recess area 27b of the recess 27 of the outer tube 21. The distance of the protrusions 39a, 39b in the circumferential direction is such that there is in the assembled state a gap G between the first protrusion 39a and an opposing sidewall of the recess 27 that serves for entering driving portions of the actuator assembly into the recess 27. The inner tube 31 may be assembled with the outer tube 21 by first introducing the lower protrusion 39b into the recess 27, rotating the inner tube 31 relative to the outer tube 21 and then entering the first protrusion 39a into the recess 27.

Referring more in detail to FIGS. 3, 4 and 6a, 6b the stopper member 300 may be provided to inhibit rotation of the tube assembly 20 relative to the polyaxial bone anchoring device 10 into a position where it can be disengaged from the polyaxial bone anchoring device 10.

The stopper member 300 includes a shaft portion 301 and a base portion 302 that encompasses the inner tube 31 approximately in a mid-portion thereof. The shaft portion 301 is received and guided in the recessed surface portion 37 of the inner tube 31. A free front end 300a of the shaft portion 301 is thickened, so that it can protrude into a channel for the rod of the polyaxial bone anchoring device 10 and block a rotational motion of the tube assembly 20 relative to the polyaxial bone anchoring device 10. In particular, the thickened portion 300a can extend into the cut-out 36 of the inner tube 31. The base portion 302 has the shape of a segment of a tube and is configured to encompass the inner tube 31 over a circumferential area. An upper edge 300b opposite to the front end 300a of the shaft portion 301 faces in the direction of the rear end 31b of the inner tube 31. In addition, a pin 303 is fixed to the base portion 302. The pin 303 has at its free end a knob-like shape that can be actuated by a user. In an assembled state of the inner tube 31 and the outer tube 21 the pin 303 protrudes out of the elongate opening 28 of the outer tube 21 as shown in FIG. 4.

Figures 6A, 6B:
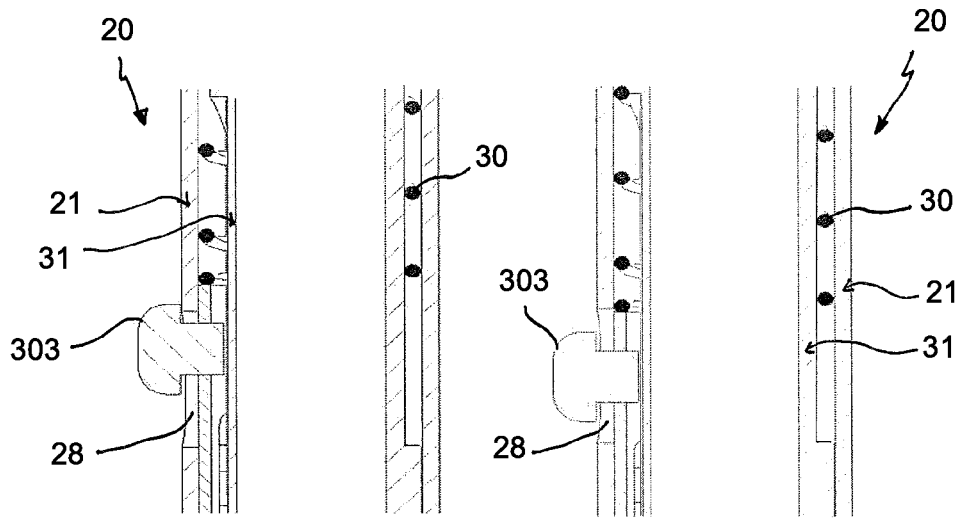
FIG. 6a shows an enlarged cross-sectional view of a portion of the tube assembly of FIGS. 3 and 4 with details of a stopper member in a first configuration.
FIG. 6b shows an enlarged cross-sectional view of a portion of the tube assembly of FIGS. 3 and 4 with details of the stopper member in a second configuration.

Referring now to FIGS. 6a and 6b, the tube assembly 20 engages an upper portion of a receiving part 5 of the polyaxial bone anchoring device 10 that comprises a recess or channel 92 for the rod. In the assembled state of the inner tube 31 and the outer tube 21, the spring member 30 is placed around the inner tube 31 between the annular protrusion 38 and the shoulder 37b. When the stopper member 300 is mounted, a lower end of the spring member 30 abuts against the upper edge 300b of the stopper member 300 and biases the stopper member 300 into its lowermost position, in which the pin 303 is close to the bottom end of the elongate opening 28 (FIG. 4 and FIG. 6b). Hence, in the lowermost position, the stopper member 300 protrudes with its thickened front end 300a into the recess 92 of the receiving part 5 and blocks rotation of the tube assembly 20 back from an engaged position to a position where the tube assembly 20 can be removed. When a user pulls the pin 303 upward, i.e. in the direction towards the rear end 31b of the inner tube 31 against the spring force of the spring member 30, the thickened end portion 300a of the stopper member no longer protrudes into the recess 92 of the receiving part 5 and the tube assembly can be rotated back to be disengaged from the polyaxial bone anchoring device 10. Thus, the stopper member 300 is arranged and biased in such a manner that it has to be actively pulled upward if the tube assembly 20 shall be removed from a polyaxial bone anchoring device 10 to which it is engaged. This enhances the safety of handling during surgery.

Next, the actuator assembly will be described referring more in detail to FIGS. 8 to 10 and 11a, 11b. The actuator assembly 40 comprises an inner sleeve 41, an outer sleeve 51, a lever assembly 61 in the form of a toggle lever, and also a handle portion 70. Referring more in detail to FIGS. 11a and 11b, the outer sleeve 51 has a front end 51a and a rear end 51b. An internal thread 52 is provided at or near the rear end 51b that allows to connect the handle portion 70 to the outer sleeve 51. An inner diameter of the outer sleeve 51 is smaller in an upper region adjacent the internal thread 52 than in a lower region adjacent to the front end 51a such that at a distance from the rear end 51b an inner shoulder 53 is formed that serves as an abutment for the inner sleeve 41. Above the inner shoulder 53, an inner protrusion 54 is formed, on each side of the longitudinal axis, i.e. there are two inner protrusions 54 offset by 180°. The protrusions 54 form second protrusions compared to the first protrusions of the tube assembly 20. They may have a substantially square-shaped contour and serve as driving portions for transferring the actuating movement of the lever assembly 61 to the tube assembly 20 as explained in detail below. The inner protrusions 54 are arranged in a circumferential direction substantially at 90° with respect to the arrangement of the lever assembly 61.

Adjacent to the rear end 51b a hinge 55 is provided that serves for attachment of one of the lever arms of the lever assembly 61, more specifically that provides one rotation point of the toggle lever. A plurality of elongate openings 57 are provided circumferentially that facilitate cleaning. In addition, an elongate slot 58 extends from the front end 51a to a distance from the front end in a direction parallel to the longitudinal axis L at the same circumferential position as the hinge 55. The slot 58 permits a hinge provided at the inner sleeve 41 to protrude therethrough.

At around 90° in a circumferential direction markings are provided that indicate a position and/or a function of the actuator assembly. For example, adjacent to the front end 51a at around 90° offset from the position of the hinge 55 in a circumferential direction a position marking 56 that may be a line that extends parallel to the longitudinal axis L, is provided that is configured to be aligned with the middle marking 200a of the position markings of the outer tube 21 of the tube assembly 20 when the actuator assembly 40 is connected to or removed from the tube assembly 20. Moreover, adjacent to the rear end 51b, function indications "LOCK", "REMOVE", "UNLOCK" may be provided, for example with additional arrows that indicate the direction of rotation to achieve a locking position, an unlocking position and a remove position of the actuator assembly 40.

The inner sleeve 41 comprises a front end 41a and a rear end 41b and has an axial length that is shorter than the axial length of the outer sleeve 51 so that the inner sleeve can be fully accommodated in the outer sleeve 51 and can abut with its rear end 41b against the inner shoulder 53 of the outer sleeve 51. The inner sleeve 41 comprises two inner protrusions 42 adjacent to its rear end 41b and offset from each other by 180°. The inner protrusions 42 are similar to the inner protrusions 54 of the outer sleeve 51, i.e. have a substantially square-shaped contour. In the assembled state the inner protrusions 42 of the inner sleeve 41 are aligned with the inner protrusions 54 of the outer sleeve 51 in the axial direction. Like the inner protrusions 54, the inner protrusions 42 are second protrusions when compared to the first protrusions 39a, 39b of the tube assembly 20 and also serve as driving portions that are configured to transfer the actuating movement of the actuator assembly 40 to the tube assembly 20.

Adjacent to the front end 41a, at the same circumferential position as the first hinge 55 of the outer sleeve 51 a second hinge 43 is provided that protrudes outward from the inner sleeve through the slot 58 in the assembled state. The second hinge 43 serves as the second rotation point of the toggle lever. At an opposite side in an axial direction, i.e. around 180° offset from the hinge 43, a spring portion 44 may be formed for example by a cut-out in the wall surface of the inner sleeve 41. At a resilient free end of the spring portion 44 a tiny pin 45 is fixed that slightly protrudes to the inside of the inner sleeve 41. The pin 45 serves for being caught in the grooves 29a, 29b, 29c in the outer wall of the outer tube 21 of the tube assembly 20 to provide a tactile and/or audible sign to a user when a respective position of the actuator assembly 40 is attained.

The lever assembly 61 comprises a first lever arm 62 that is hingedly connected at one end via a pin 63 to the second hinge 43 provided at the inner sleeve 41. A longer end portion or grip portion 62a of the first lever arm 62 has a gripping structure at its side facing away from the sleeves 41, 51 to facilitate actuation with the hand. A second lever arm 64 of the lever assembly 61 is on one side hingedly connected via a pin 65 to the first hinge 55 and at its second end via a pin 66 hingedly connected to the first lever arm 62. The latter connection provides the third rotation point of the toggle lever. In the embodiment, the second lever arm 64 is shorter than the first lever arm 62. The first lever arm 62 has a slightly angled shape. More specifically, as depicted in FIGS. 11a and 11b, a length of the grip portion 62a of the first lever arm 62 is such that the height position of the first lever arm substantially corresponds to the height position of the handle portion 70. Moreover, the first lever arm 62 comprises a pin 67 that extends in a direction transverse to the grip portion 62a and that is located above the third rotation point defined by the pin 66. The transversely extending pin 67 protrudes inward, i.e. towards the second lever arm 64, and may assist to push the second lever arm 64 into the straight position as seen in FIG. 11b.

The handle portion 70 has a threaded projection 72 that allows it to be screwed into the first sleeve 51. The handle portion 70 may further comprise a gripping structure 73 such as circumferential lobes or crests that facilitates gripping. A plurality of through-holes 74 may also be provided to facilitate cleaning.

Referring again to FIGS. 11a and 11b, in the assembled state of the inner sleeve 41 and the outer sleeve 51, a second spring member 50, for example a coil spring is inserted into the outer sleeve 51 and is supported on one side by an annular ring 59, for example a split ring, that may be held in an annular groove near the front end 51a of the outer sleeve 51. On the other side, the spring member 50 abuts against the front end 41a of the inner sleeve 41. The spring member 50 is configured to bias the inner sleeve 41 against the inner shoulder 53 of the outer sleeve 51 as depicted in FIG. 11a. In this configuration, the lever assembly 61 is in the angled configuration where the first lever arm 62 and the second lever arm 64 are angled with respect to each other and the grip portion 62a extends in an angled manner away from the handle portion 70. This configuration is a default configuration due to the biasing of the second spring member 50. The inner protrusions 54 and 42 are adjacent to each other in an axial direction.

When the first lever arm 62 is pushed towards the handle portion 70, the lever assembly assumes the straight configuration, where the first lever arm 62a and the second lever arm 64 are more parallel or less angled as shown in FIG. 11b. The inner sleeve 41 is pushed downward towards the front end 51a of the outer sleeve 51 whereby the inner protrusions 54 and 42 move away from each other such that a distance d is between them in an axial direction.

The instrument is made of a body-compatible material. In particular, titanium or stainless steel may be such a suitable material, but other materials could also be used as long as they are body-compatible.

Referring now again to FIGS. 1, 2 and 7a, 7b, the mounting of the tube assembly 20 and the actuator assembly 40 and the actuation of the tube assembly 20 by the actuator assembly 40 will be explained. Mounting of the actuator assembly is effected as follows. The inner tube 31 is within the outer tube 21 and the second protrusions 39a, 39b are in the respective recess areas 27a, 27b of the recess 27 of the outer tube. The position marking 200a that indicates the REMOVE position, is at a circumferential position that corresponds to the gap G between the wall of the recess 27 and the first protrusion 39a. The actuator assembly 40 which is in the default configuration of FIG. 11a is mounted onto the tube assembly 20 in such an orientation that the position marking 56 is in line with the position marking 200a. This permits the second protrusions 54, 42 to pass downward through the gap G between the first protrusion 39a and the sidewall of the recess 27 at the tube assembly 20 when the actuator assembly 40 is moved onto the tube assembly 20. Removing is effected in the same position. The second protrusions 54, 42 move upwards through the gap G.

Figures 7A, 7B:
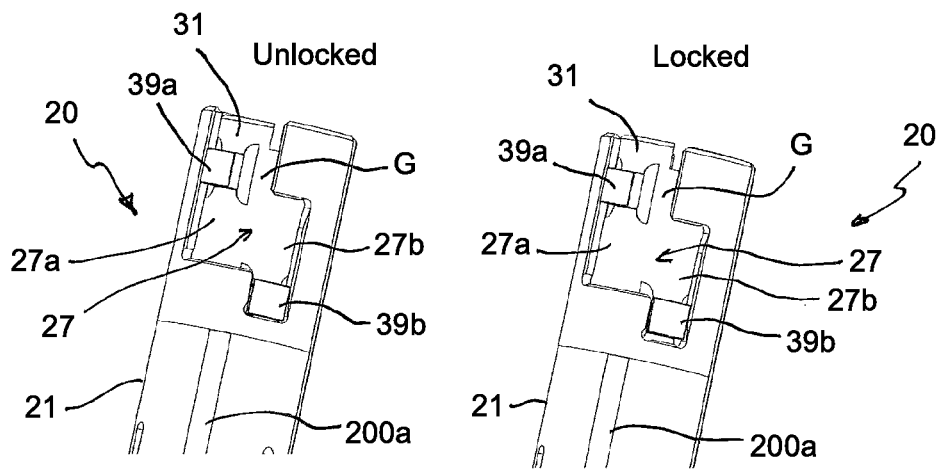
FIG. 7a shows an enlarged perspective view of an upper portion of the tube assembly of FIG. 4 in a first configuration.
FIG. 7b shows an enlarged perspective view of an upper portion of the tube assembly of FIG. 4 in a second configuration.
Figure 8:
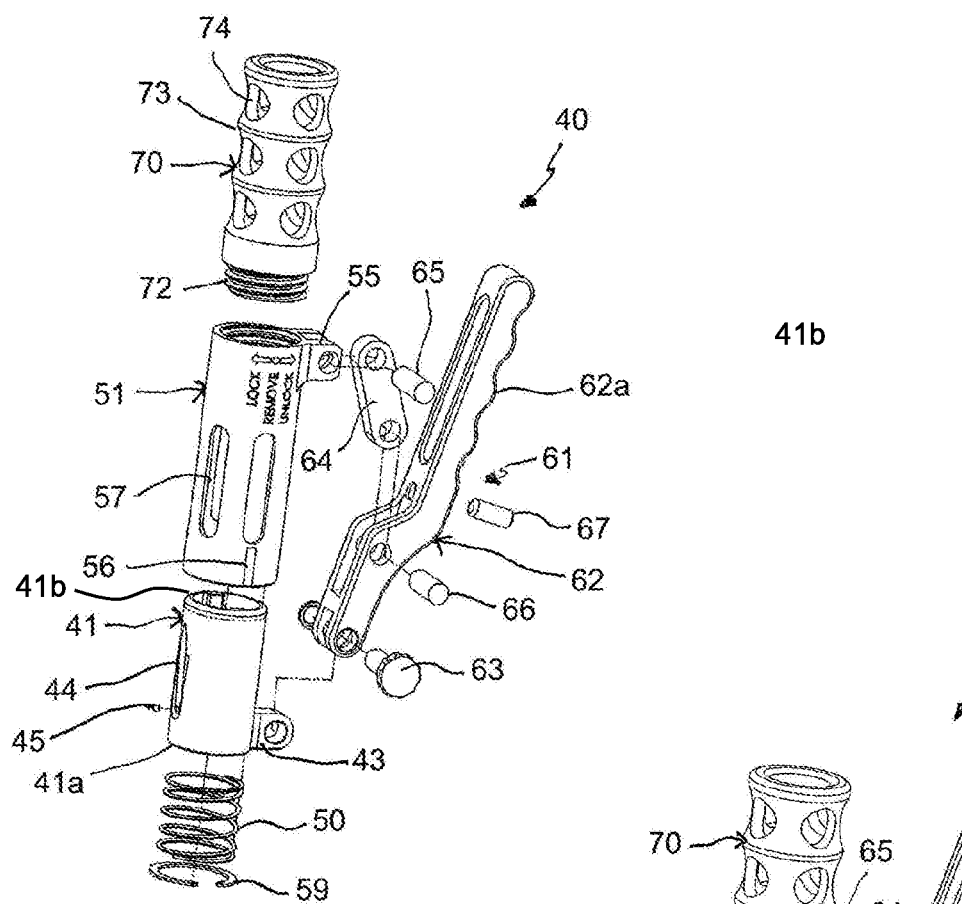
FIG. 8 shows an exploded perspective view of an actuator assembly of the instrument according to the embodiment.
Figure 9:
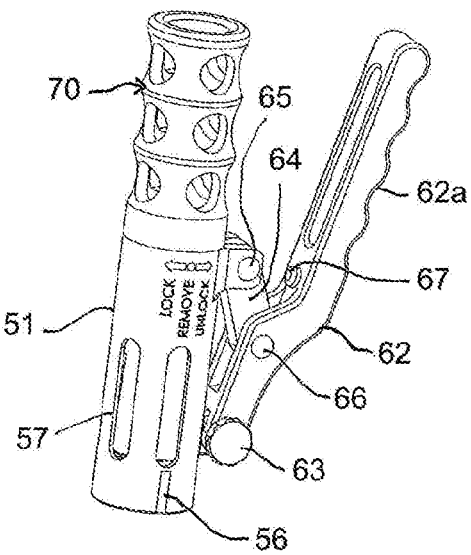
FIG. 9 shows the actuator assembly of FIG. 8 in an assembled state in an angled configuration of a lever assembly that is part of the actuator assembly.

The locking configuration of the instrument is attained as follows. When the actuator assembly 40 is rotated in the clockwise direction, such that the position marking 56 is aligned with the position marking 200c indicated with "LOCK" the second protrusions 54, 42 of the actuator assembly 40 move into the recess area 27a (e.g., circumferentially away from the recess area 27b and below the first protrusion 39a). When the lever is actuated by pressing the first lever arm 62 in the direction of the handle portion 70 so that the straight configuration (FIG. 11b) is attained, the second protrusions 54, 42 become spaced apart from each other as previously explained with respect to FIG. 11b, thereby leaving a gap d between them in axial direction. As the wall of the recess 27 provides an abutment for the second protrusion 42 of the inner sleeve 41, the second protrusion 54 of the outer sleeve 51 presses the first protrusion 39a of the inner tube 31 upward towards the rear end 21b of the outer tube 21 and the first protrusion 39b also moves upward with respect to the outer tube (FIG. 7b). As a consequence, the front ends 21a, 31a of the tubes are axially displaced with respect to each other such that the distance between the engagement portions of the inner and outer tubes becomes larger.

The unlocking configuration is attained by rotating the actuator assembly 40 in the default configuration in a counter-clockwise direction such that the position marking 56 is aligned with the position marking 200b indicated with "UNLOCK". The second protrusions 54, 42 enter the second recess area 27b. Pushing the lever arm 62 spreads the second protrusions 54, 42 apart from each other so that the second protrusion 42 of the inner sleeve 41 pushes down the first protrusion 39b of the inner tube 31. The opposite border of the recess 27 serves as an abutment for the second protrusion 52 of the outer sleeve 51 (FIG. 7a). As a consequence, the front ends 21a, 31a of the tubes are axially displaced with respect to each other such that the distance between the engagement portions of the inner and outer tubes becomes smaller.

Figure 12:
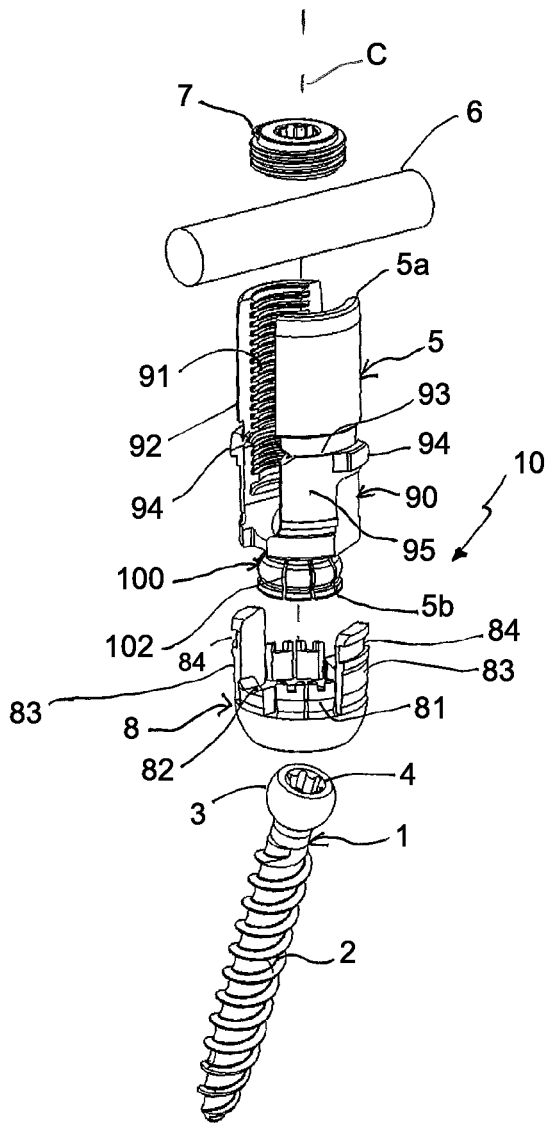
FIG. 12 shows an exploded perspective view of a polyaxial bone anchoring device according to an embodiment.
Figure 14:
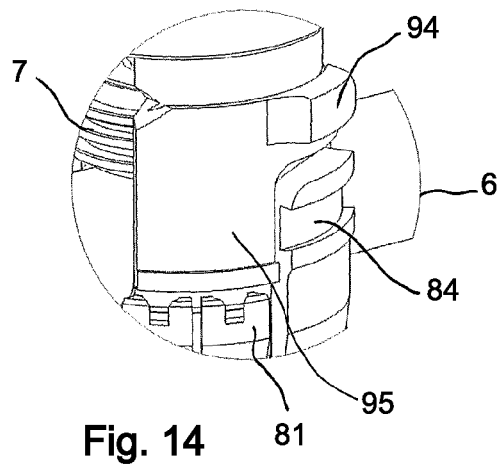
FIG. 14 shows an enlarged perspective view of a detail of FIG. 13.
Figure 13:
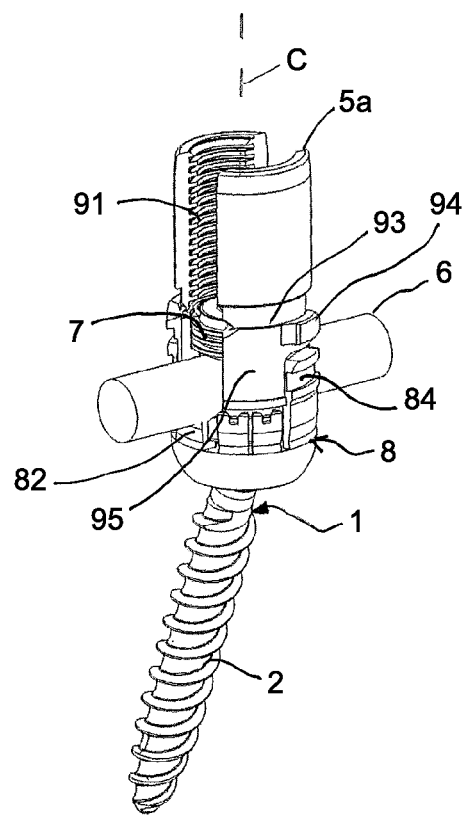
FIG. 13 shows a perspective view of the polyaxial bone anchoring device of FIG. 12 in an assembled state.

Next, with reference to FIGS. 12 to 14, a polyaxial bone anchoring device that is suitable for use with the instrument, will be explained. The polyaxial bone anchoring device 10 according to an embodiment comprises a bone anchoring element 1 with a shank 2 and a head 3 with a spherically-shaped outer surface portion. The bone anchoring element 1 may be a bone screw with a threaded shank. The head 3 may have a recess 4 is provided for engagement with a tool, such as a driver. A receiving part 5 is provided for receiving the head 3 and connecting the bone anchoring element via the head 3 to a rod 6. In addition, a fixation element 7 in the form of an inner screw or a set screw may be provided for fixing the rod 6 in a receiving part 5. Also, the bone anchoring device 10 includes a locking ring 8 for the locking head 3 in the receiving part 5.

The receiving part 5 has a first or upper end 5a and a second or lower end 5b. Adjacent to the upper end 5a, a rod receiving portion 90 is provided and adjacent to the lower end 5b a head receiving portion 100 is provided. The rod receiving portion 90 is substantially cylindrical and comprises a coaxial bore 91 that extends from the upper end 5a into the head receiving portion 100. The bore 91 comprises an internal thread in at least a region thereof for receiving the fixation element 7. A substantially U-shaped recess 92 that forms a channel for receiving the rod 6 extends from the upper end 5a to almost the beginning of the head receiving portion 100. At a distance from the upper end 5a a groove or otherwise weakened section 93 is provided that allows to break-off the upper portions of the receiving part formed by the U-shaped recess that serve as extended tabs. By means of the long extended tabs it is possible to manipulate the polyaxial bone anchoring device with an inserted rod 6 that is at a higher position compared to the final position so that, for example, a vertebra can be pulled against the rod.

At an outer surface of the rod receiving portion 90 an engagement structure for engagement with the tube assembly is provided. The engagement structure may comprise circumferentially extending ribs 94. The ribs 94 are arranged asymmetrical with respect to a plane including a central axis C of the receiving part and a channel axis of the substantially U-shaped recess 92. That means, a first rib 94 starts at the U-shaped recess 92 on one side and extends to a distance around the receiving part and the second rib 94 starts at the opposite side of the U-shaped recess relative to the central axis C and extends from there to a distance around the receiving part 5. Thereby, a rib-free surface 95 is formed on each side from the U-shaped recess.

The head receiving portion 100 has a substantially cap-like shape with a hollow substantially spherical interior portion 101 (see FIGS. 16a to 16c) for receiving the head 3 pivotably therein. A plurality of slits 102 render the head receiving portion flexible so that when pressure is exerted onto the head receiving portion by the locking ring 8, the head 3 can be clamped and finally locked.

The locking ring 8 is designed to encompass the head receiving portion and has an internal surface structure that allows to achieve in corporation with the head receiving portion a full locking of the head 3 in the head receiving portion 100 when the locking ring in its lowermost position and a pre-locking when the locking ring is in a position slightly above the lowermost position which still allows pivoting of the head 3 in the head receiving portion but prevents removal of the head 3 from the head receiving portion 100. The locking ring 8 further has a plurality of upstanding flexible sections 81 that may serve for engagement with a receiving part to preliminarily hold the locking ring in a pre-locking position. Also, two opposite projections 82 are provided at an upper side of the locking ring that serve for supporting the rod 6. In the embodiment shown, the locking ring 8 also comprises two upstanding arms 83 that are positioned asymmetrically with respect to a plane that extends through the central axis C and through the middle of the rod support projections 82 in the same manner as the ribs 94 of rod receiving portion 90 are arranged. At an upper end of the arms 83 an engagement structure in the form of grooves 84 is provided that is configured to be engaged by the tube assembly 20 of the instrument. As depicted in FIGS. 13 and 14, in the assembled state, the engagement structure in the form of the ribs 94 on the receiving part and the engagement structure in the form of the grooves 83 is aligned, leaving the rib-free surface 95 of the head receiving portion 90 exposed. The upstanding arms 83 of the locking ring with the engagement structure 84 at or near their upper end facilitate finding of the engagement structure with the instrument.

In the following, use of the instrument will be explained. Referring first to FIGS. 15a to 15c, the steps of attaching the instrument to the polyaxial bone anchoring device are illustrated. The bone anchoring element may be implanted in a vertebra or other bone. The locking ring 8 is in an axial position in which it does not fully lock the head but the head 3 is prevented from removal from the head receiving portion 100. The rod 6 is inserted into the substantially U-shaped recess 92. Also, the fixation element 7 may be already screwed into the bore 91 of the receiving part 5.

Due to the extended tabs, the rod is still movable not only along the rod axis but also in an axial direction. The engagement portions 25 of the outer tube 21 and 35 of the inner tube 31 have their closest distance from each other which is defined by an abutment of the front portion 31a of the inner tube 31 against the inner shoulder 26 of the outer tube. The stopper member 300 is in the default position that means it is protruding downward in the cutout 36 (see FIG. 3). In this configuration, the instrument is moved downward so that the front portions 31a of the inner tube 31 and 21a of the outer tube are directed towards the rib-free outer surface portion 95 of the receiving part 5.

Next, as shown in FIG. 15b, the front portions of the tube assembly 20 of the instrument move along the rib-free surface portions 95 of the receiving part 5 to a position where the engagement portions in form of the ribs 25 of the outer tube and the grooves 35 of the inner tube 31 are on the same axial position as the corresponding engagement portions in the form of the grooves 84 of the locking ring and the ribs 94 of the receiving part 5. At the same time, the stopper member 300 is retracted by pulling upwards of the pin 303 (not shown).

As depicted in FIG. 15c, the instrument is then rotated so that the engagement portions at the instrument and the engagement portions at the locking ring and the receiving part engage. More in detail, the rib 25 at the outer tube engages the groove 84 at the locking ring and the rib 94 at the receiving part 5 engages the grooves 35 at the inner tube 31. After engagement, the stopper member 300 can be released so that it is biased downward and the thickened end portion 300a protrudes into the U-shaped recess 92 of the receiving part 5. There, the thickened end portion 300a of the stopper member 300 abuts against the sides of the U-shaped recess 92. If for some reason a user tries to rotate back the instrument out of the engagement with the receiving part and the locking ring, such back-rotation is prevented by the stopper member 300. This enhances the safety of the device during surgery. For disengagement of the tube assembly 20, the stopper member 300 may be retracted so that the instrument can be rotated back out of engagement and removed along the rib-free portions 95 of the receiving part 5.

Referring now to FIGS. 16a to 16c, the function of locking and unlocking of the head 3 in the head receiving portion 100 of the receiving part with the instrument will be explained. In FIG. 16a, the instrument is in the engaged configuration of FIG. 15c where the engagement portions of the outer tube engage the engagement portions of the locking ring and the engagement portions of the inner tube engage the engagement portions of the receiving part. The locking ring 8 is in an upper position in an axial direction where the head 3 is still pivotable in the head receiving portion but is prevented from removal from the head receiving portion 100. The line 500 indicates a bone surface. The front portions of the inner tube 31 and the outer tube 21 of the tube assembly have their smallest distance from each other. The actuator assembly is in a configuration "UNLOCKED". In this configuration, adjustments of the angle of the receiving part and the locking ring relative to the bone anchoring element 1 can be performed with the instrument.

FIG. 16b depicts a locking position of the locking ring 8. In the locking position, the locking ring 8 is moved downward so that it fully clamps and locks the head 3 in the head receiving portion 100. This is achieved by moving downward the locking ring 8 with the outer tube 21 that is driven downward by the actuator assembly 40 when the actuator assembly 40 is in a configuration "LOCKED". As can be seen, the distance between the engagement portions of the receiving part 5 and the locking ring 8 has been increased. The front portion 31a of the inner tube 31 no longer abuts against the inner shoulder 26 of the outer tube 21. In the locked configuration, it is possible to pull the associated vertebra for a bone 500 upward with the instrument towards the inserted rod 6.

Finally, as shown in FIG. 16c, the fixation element 7 can be tightened to fix the locked configuration.

Referring now to FIGS. 17a to 17e, the handling of the actuator assembly corresponding to locking and unlocking of the head 3 in the head receiving portion 100 will be explained. As depicted in FIG. 17a, to obtain the locked configuration, the actuator assembly 40 is rotated in a clockwise direction in its default configuration, where the lever system 61 is in the angled configuration. When the position marking 56 is aligned with the position marking 200c for the locked configuration, the lever arm is pushed with the hand against the grip portion 70 as shown in FIG. 17b to achieve locking of the head 3, as shown in FIG. 16b.

To release the locked configuration, the lever arm 61 of the actuator assembly 40 is no longer pushed against the grip portion so that it returns to the default configuration as shown in FIG. 17c. Then, the actuator assembly 40 can be rotated in the counter-clockwise direction as shown in FIG. 17d until the position marking 56 of the actuator assembly 40 is aligned with the position marking 200b on the outer tube as depicted in FIG. 17d. Next, as shown in FIG. 17e, the lever arm 61 is pushed against the grip portion 70 so that the toggle lever attains the straight configuration to achieve unlocking of the head 3 as shown in FIG. 16a.

Each time when the actuator assembly 40 is rotated into one of the positions "LOCK", "UNLOCK" or "REMOVE", the tiny pin 45 of the spring 44 of the inner tube 41 comes to rest in a corresponding groove 29c, 29b, 29a of the outer tube 21 (FIG. 3) and produces a tactile or audible sign that indicates to the user that the respective position is reached.

Figure 18:
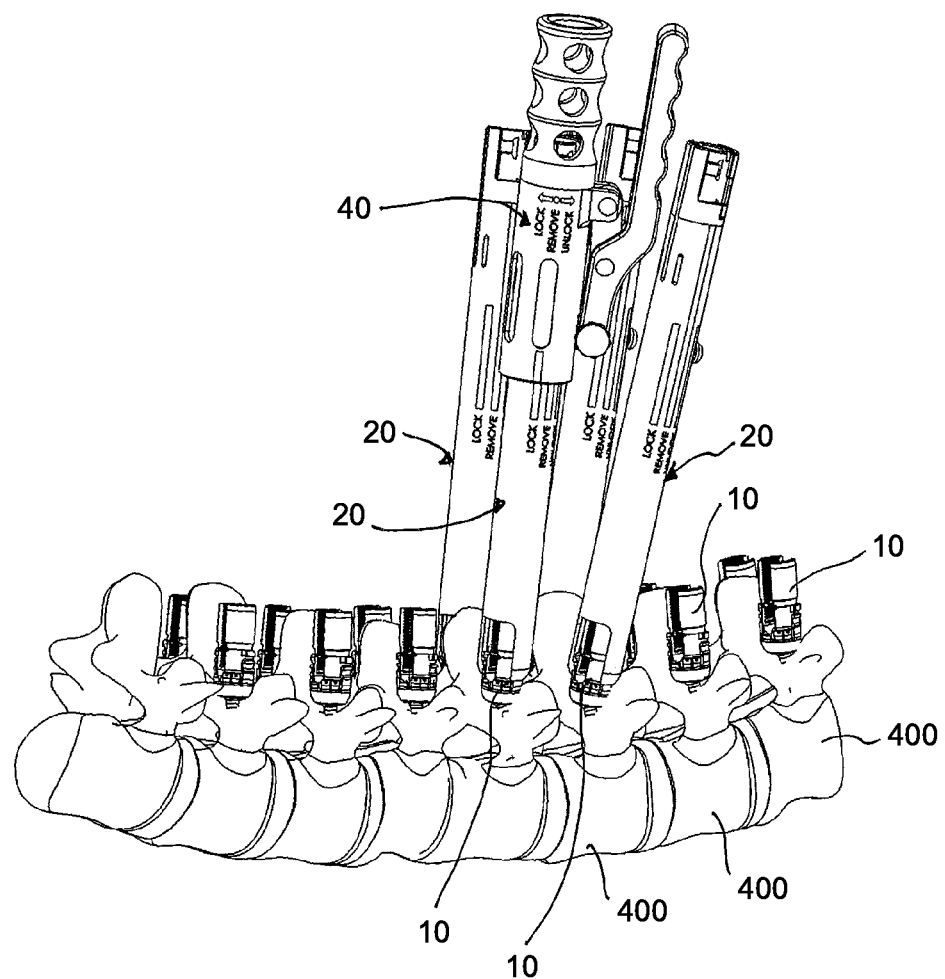
FIG. 18 shows a perspective view of a spinal column with a plurality of polyaxial bone anchoring devices and a plurality of tube assemblies connected to polyaxial bone anchoring devices and one single actuator assembly according to an embodiment.

Turning now to FIG. 18, a plurality of polyaxial bone anchoring devices 10 as described above are shown implanted in respective vertebrae 400. The rod 6 (not shown) may be inserted. Tube assemblies 20 are connected to polyaxial bone anchoring devices. Several steps of positioning and re-positioning of the receiving parts can be performed using one single actuator assembly 40 that is selectively connectable with the different tube assemblies 20. As the actuator assembly 40 is easy to handle, the time for the adjustment steps when a plurality of bone anchoring devices have to be adjusted, may be shortened. The space needed with the instrument can be reduced.

Various modifications can be contemplated. For example, the arrangement, number, configuration, and shape of the protrusions that form the driving and the driven portions may be different. Although the instrument is shown together with a polyaxial bone anchoring device of the bottom loading type with an outer locking ring, the instrument is not limited to be used only with such a device. For example, the instrument can be used with any type of polyaxial bone anchoring device in which a clamping means is axially displaceable to clamp an inserted head.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An instrument for locking and unlocking a head of a bone anchor relative to a receiving part of a polyaxial bone anchoring device, the instrument comprising:
    a tube assembly having a longitudinal axis and comprising an inner tube and an outer tube positionable at least partially around the inner tube;
    wherein the inner tube is displaceable relative to the outer tube between a first axial position configured to unlock the bone anchoring device such that the head is pivotable relative to the receiving part, and a second axial position configured to lock the head relative to the receiving part; and
    an actuator movable in a first direction from a first orientation to a second orientation to axially displace the inner tube and the outer tube relative to one another;
    wherein the inner tube is movable from the first axial position towards the second axial position when the actuator is moved in the first direction, and
    wherein the inner tube is further movable from the second axial position back towards the first axial position when the actuator is moved in the first direction.

2. The instrument of claim 1, wherein the actuator is on an actuator assembly, and at least part of the actuator assembly is movable relative to the tube assembly, to adjust the actuator assembly between a first configuration for locking the bone anchoring device and a second configuration for unlocking the bone anchoring device.

3. The instrument of claim 2, wherein the actuator assembly is removably connectable to the tube assembly.

4. The instrument of claim 3, wherein the at least part of the actuator assembly is rotatable around the longitudinal axis relative to the tube assembly, to adjust the actuator assembly between the first configuration and the second configuration, and wherein the at least part of the actuator assembly is further rotatable to a third configuration wherein the actuator assembly is connectable to and/or removable from the tube assembly.

5. The instrument of claim 1, wherein the actuator comprises a lever, and wherein the first orientation corresponds to a first position of the lever and the second orientation corresponds to a second position of the lever.

6. The instrument of claim 1, wherein the actuator is on an actuator assembly, and the actuator assembly comprises an outer sleeve and an inner sleeve that are axially displaceable relative to one another when the actuator is adjusted between the first and second orientations.

7. The instrument of claim 6, wherein the actuator comprises a toggle lever comprising a first lever arm hingedly connected to the outer sleeve and a second lever arm hingedly connected to the inner sleeve.

8. The instrument of claim 1, wherein the actuator is on an actuator assembly, and the actuator assembly comprises a spring member that biases the actuator towards the first orientation.

9. The instrument of claim 1, wherein the actuator comprises a grip portion to facilitate exerting of a counter force when the actuator is moved from the first orientation to the second orientation.

10. The instrument of claim 1, further comprising a stopper member movable along the longitudinal axis of the tube assembly between a first position wherein a rotational movement of the tube assembly relative to a connected polyaxial bone anchoring device is restricted, and a second position wherein the rotational movement of the tube assembly relative to the connected polyaxial bone anchoring device is not restricted.

11. A system comprising:
    a polyaxial bone anchoring device comprising a bone anchor for anchoring in a bone, a receiving part for receiving a head of the bone anchor, and a clamping device configured to clamp the head to lock the head relative to the receiving part; and
    an instrument connectable to the bone anchoring device to lock and unlock the head relative to the receiving part, the instrument comprising an actuator movable in a first direction from a first orientation to a second orientation,
    wherein the clamping device is movable relative to the receiving part, from a first position where the head is pivotable relative to the receiving part towards a second position where the head is locked relative to the receiving part, when the actuator is moved in the first direction, and
    wherein the clamping device is further movable from the second position back towards the first position when the actuator is moved in the first direction.

12. The system of claim 11, wherein the actuator comprises a lever, and wherein the first orientation corresponds to a first position of the lever and the second orientation corresponds to a second position of the lever.

13. The system of claim 11, wherein the actuator is on an actuator assembly, and the actuator assembly comprises an outer sleeve and an inner sleeve that are axially displaceable relative to one another when the actuator is moved in the first direction.

14. The system of claim 13, wherein the actuator comprises a toggle lever comprising a first lever arm hingedly connected to the outer sleeve and a second lever arm hingedly connected to the inner sleeve.

15. The system of claim 11, wherein the instrument further comprises a tube assembly having a longitudinal axis and positionable between the actuator and the bone anchoring device, the tube assembly comprising an inner tube and an outer tube positionable at least partially around the inner tube, and
    wherein the actuator is configured to move the inner tube relative to the outer tube between a first axial position where the clamping device assumes the first position relative to the receiving part and a second axial position where the clamping device assumes the second position relative to the receiving part.

16. The system of claim 15, wherein the actuator is on an actuator assembly, and at least part of the actuator assembly is rotatable around the longitudinal axis relative to the tube assembly, to adjust the actuator assembly between a first configuration for locking the bone anchoring device and a second configuration for unlocking the bone anchoring device.

17. The system of claim 11, wherein the receiving part comprises a rod receiving portion defining a recess for receiving the rod, and a head receiving portion for accommodating the head of the bone anchor, the head receiving portion being expandable for inserting and clamping the head.

18. The system of claim 17, wherein the clamping device comprises a locking ring positionable around the head receiving portion.

19. A method for using an instrument to lock and unlock a polyaxial bone anchoring device comprising a bone anchor, a receiving part for receiving a head of the bone anchor, and a clamping device for clamping the head, the method comprising:
  inserting a shank of the bone anchor into a bone;
  connecting the instrument to the bone anchoring device when the head is held in the receiving part;
  adjusting an angular position of the receiving part relative to the head;
  moving an actuator of the instrument in a first direction from a first orientation towards a second orientation to move the clamping device from a first position where the angular position of the receiving part remains adjustable relative to the head towards a second position where the receiving part is locked relative to the head; and
  moving the actuator of the instrument in the first direction to move the clamping device from the second position back towards the first position to unlock the receiving part relative to the head.

20. The method of claim 19, further comprising:
  readjusting the angular position of the receiving part relative to the head after using the instrument to unlock the receiving part relative to the head;
  connecting a rod to the receiving part; and
  connecting a fixation element to the receiving part to lock the rod relative to the receiving part and to lock the angular position of the receiving part relative to the head.

* * * * *